United States Patent
Christoudias

(10) Patent No.: US 6,391,040 B1
(45) Date of Patent: May 21, 2002

(54) CHRISTOUDIAS ENDODISSECTOR

(76) Inventor: George C. Christoudias, 17 Lower Cross Rd., Saddle River, NJ (US) 07548

(*) Notice: Subject to any disclaimer, the term of this patent is extended or adjusted under 35 U.S.C. 154(b) by 0 days.

(21) Appl. No.: 09/440,181

(22) Filed: Nov. 15, 1999

(51) Int. Cl.[7] .................................................. A61F 9/00
(52) U.S. Cl. ..................................................... 606/162
(58) Field of Search ................................ 606/161, 162, 606/160, 131; 15/106–114; 433/142, 141, 147; 601/139; 132/309

(56) References Cited

U.S. PATENT DOCUMENTS 1,980,826 A * 11/1934 Reiss .......................... 606/161
2,651,068 A * 9/1953 Seko ........................... 606/161
5,931,845 A * 8/1999 Amyette ...................... 606/162

* cited by examiner

Primary Examiner—Kevin T. Truong
(74) Attorney, Agent, or Firm—Richard A. Joel, Esq.

(57) ABSTRACT

An endodissector for dissecting, wiping and cleaning tissues during laparoscopic or conventional surgery comprises an elongated or tubular instrument having a one piece molded, solid or tubular plastic mesh tip at one end and an elongated body comprising a handle at the other end. The tip is mounted on a frame and includes a threaded base extending downwardly to engage a threaded receptacle in the elongated body. The frame and mesh tip may include a straight central lumen for the insertion and use of laparoscopic instruments. Optionally, the frame may include a side port coupled to the lumen for irrigation purposes.

3 Claims, 3 Drawing Sheets

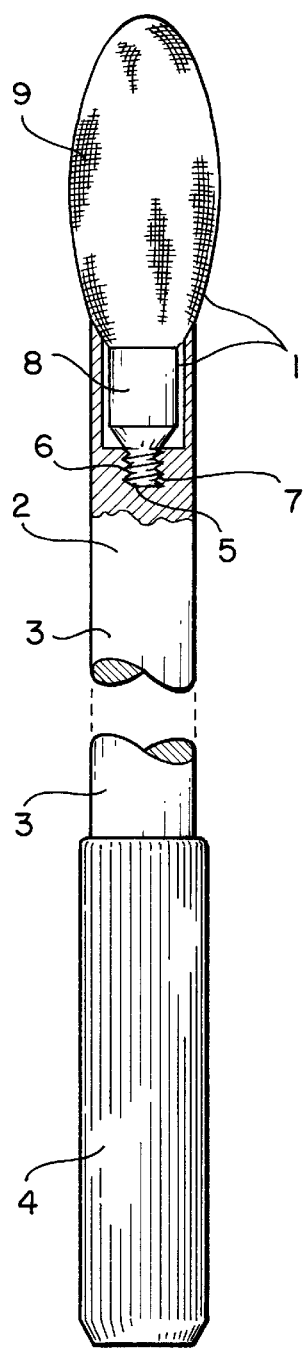
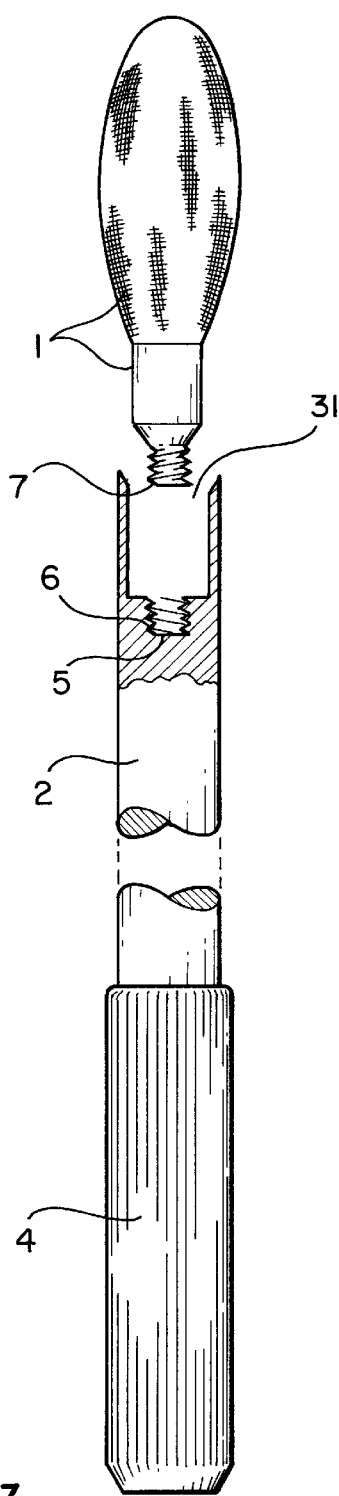
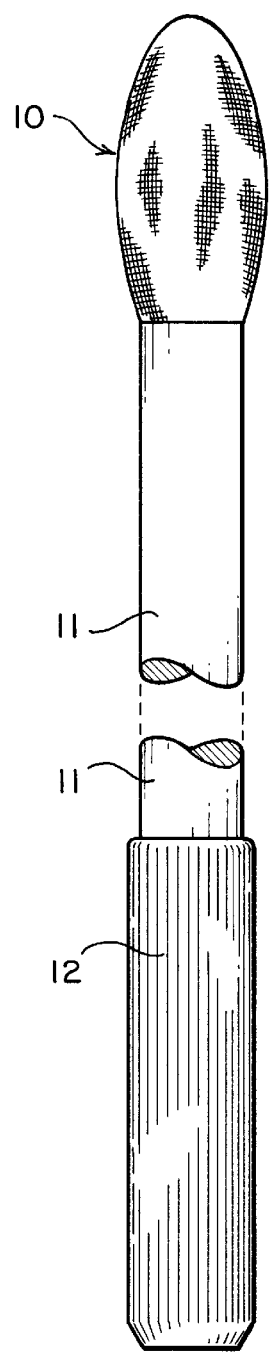
FIG. 1
FIG. 1a
FIG. 2

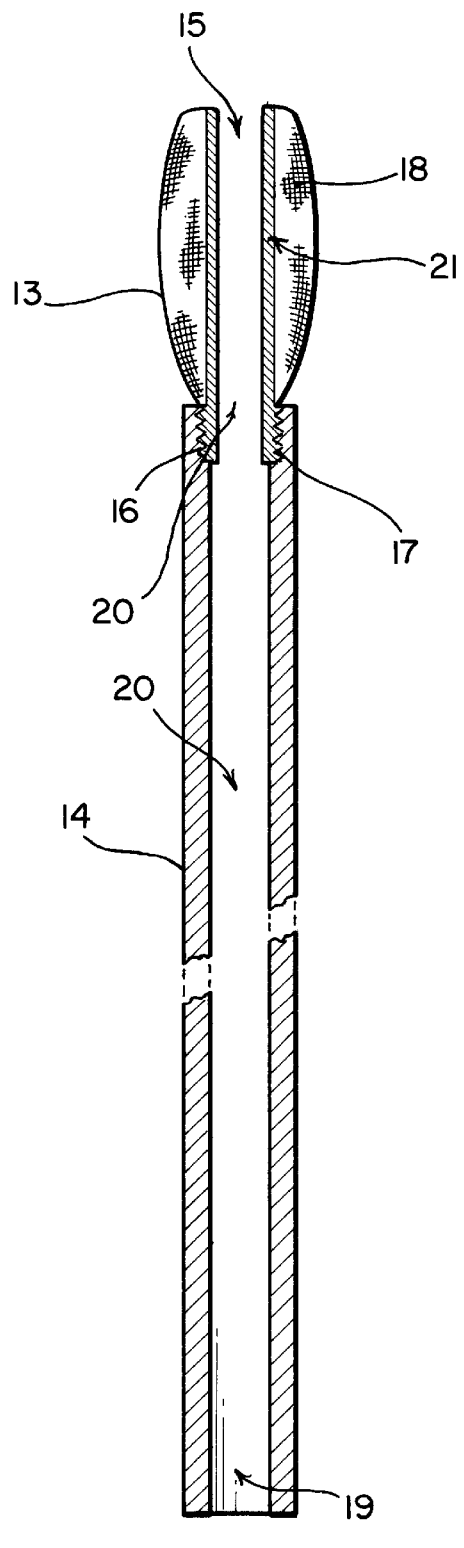
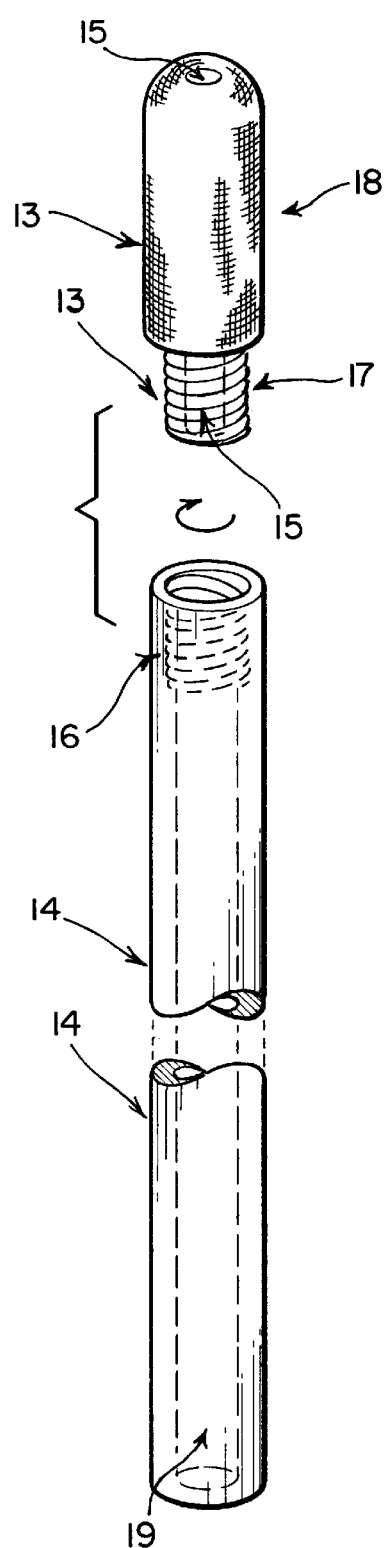
FIG. 3
FIG. 4

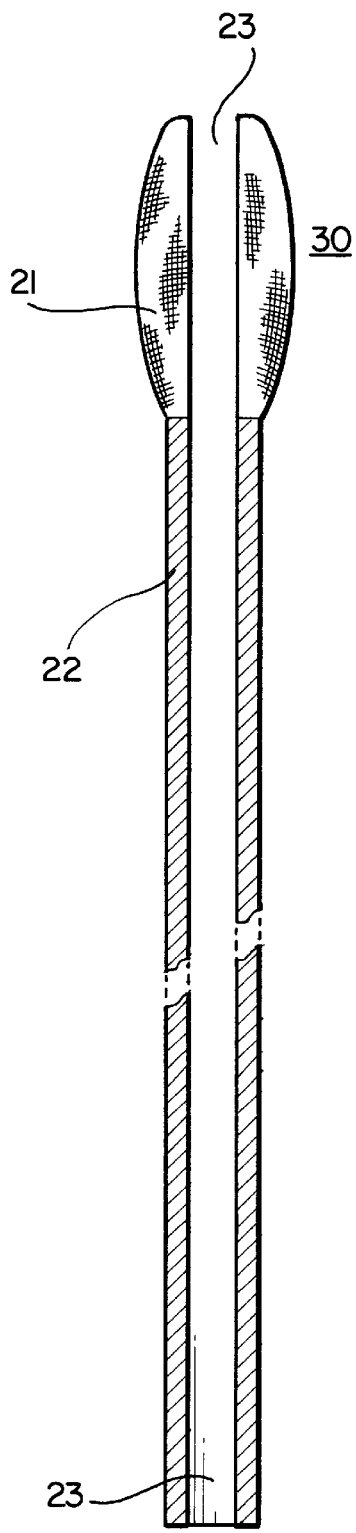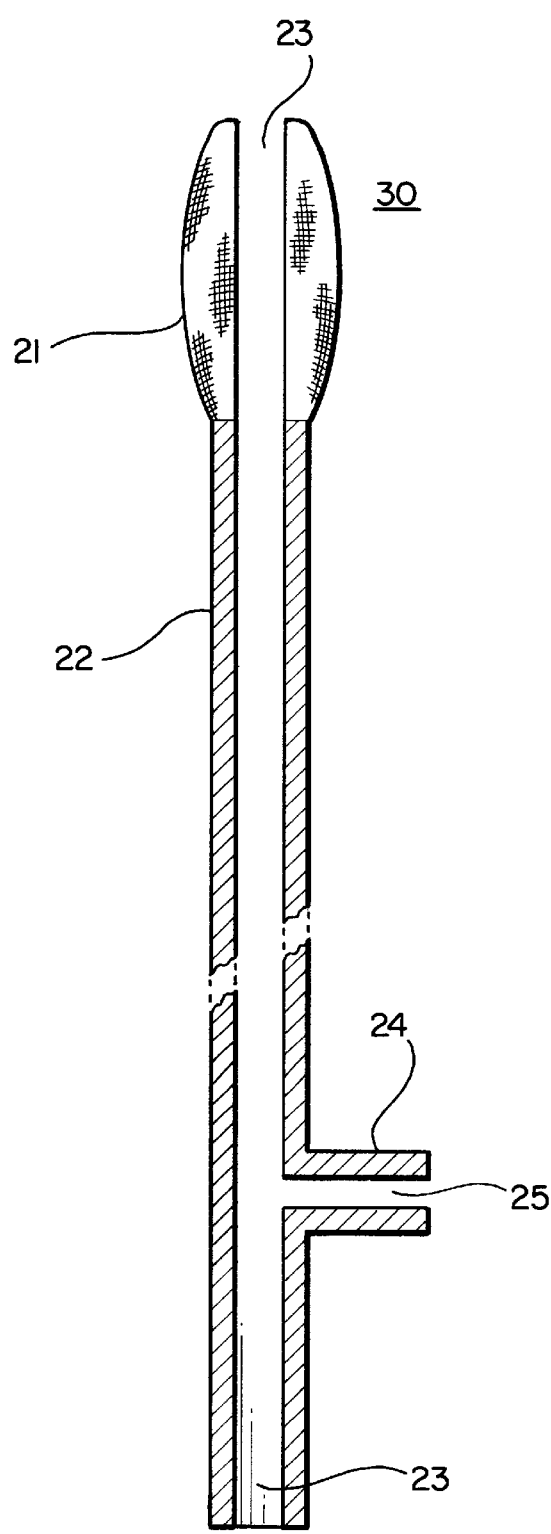

CHRISTOUDIAS ENDODISSECTOR

CROSS-REFERENCE TO RELATED APPLICATIONS

This application is an improvement on applicant's U.S. Pat. No. 5,688,230 filed Apr. 5, 1995 and U.S. Pat. No. 5,817,121 filed on Oct. 6, 1998.

STATEMENT REGARDING FEDERALLY SPONSORED RESEARCH OR DEVELOPMENT

There are no statements regarding Federally-sponsored research or developments.

BACKGROUND OF THE INVENTION

1. Field of the Invention

This invention comprises a new and improved instrument for dissecting, separating, wiping or cleaning tissues during the performance of endoscopic surgery.

2. Description of the Related Art Including Information Disclosed Under 37 CFR §§1.97–1.98.

The number of laparoscopic procedures is steadily increasing as more and more surgeons are becoming accustomed to the endoscopic modality of operating. Indeed, numerous new instruments and devices have been introduced and are being used to facilitate the performance of endoscopic operations. With the broadening spectrum of procedures being performed, there is increased demand for more specialized instruments. In response to this demand, the present invention discloses a new specialized instrument for dissecting tissues during endoscopic surgery which is a variation on the Christoudias endodissector disclosed in U.S. Pat. No. 5,817,121.

In the prior art, an instrument with similar functions has been used extensively in conventional surgery and is known as a "peanut" and/or "dissector." This "peanut" or "dissector" is comprised of mesh gauze shaped in the form of a ball which is marketed as "weck-sorb" or "pilling weck."

This ball shaped mesh gauze is grasped firmly by the end portions or tip of any commonly used surgical clamp such as a "Kelly Clamp," "tonsil clamp," "hemostat," etc. and by manipulating the clamp, the ball shaped mesh gauze is used for dissection, cleaning, sponging and/or wiping the target tissues. While this "dissector" is suitable for conventional surgery, it cannot be used in laparoscopic surgery since there is a limit on the dimensions of the instrument with the mesh gauze ball that can pass through a standard endoscopic port. This precludes the use of conventional surgical instruments for these purposes. On the other hand, the use of the laparoscopic graspers currently available for these functions are both difficult to use and often dangerous. The graspers are difficult to use because the grasping surface is neither suitable nor strong enough to close firmly on the gauze ball thus leaving the jaws partially open and therefore generally too bulky to go through the port. If the laparoscopic grasper with the gauze ball did go through the port, it is possible that due to the imperfect grasp, the mesh gauze ball could escape from the instrument and become lost in the abdomen. Endless amounts of time would then have to be consumed to find and retrieve the mesh ball to avoid life threatening consequences.

A disposable laparoscopic "peanut" manufactured by U.S. Surgical under the name of Endopeanut consists of a long stem having a piece of mesh gauze rolled and fixed in place over one end. The functioning gauze end is cylindrical and is lacking in strength and uniformity; it is not nearly as strong and easy to manipulate as the open conventional surgery "peanut" or "dissector."

There are significant differences between the Christoudias Endodissector and the Dodson "Irrigator-Aspirator, Blunt Dissector" disclosed in U.S. Pat. No. 5,205,816. Dodson describes "A laparoscopic medical instrument for performing blunt dissection as well as irrigator and aspirator." It is obvious that the Dodson instrument has no working port through which a cautery electrode, scissors or grasper can be inserted and used as described by the applicant in Claims 4 and 5.

A significant difference is that the Dodson instrument has no working port. It is specifically stated that the function of his instrument, (column 1, lines 9, 10, 100) is an irrigator aspirator and blunt dissector. There is no reference or description in Dodson's text, drawings or claims that show any intent or feature that will allow the use of any laparoscopic instrument through the lumen of his irrigator, aspirator, or blunt dissector. In the summary of his invention, Dodson describes the use of a Luer fitting which is press fit over the proximal end of his instrument connecting it to suction and irrigation. No laparoscopic instrument currently in use can fit through a Luer lock that is currently used in a standard operating room.

The present invention is intended to fill this void by providing an endoscopic instrument of the type disclosed in FIGS. 10, 11a, 16, 17, 22c and 23 in U.S. Pat. No. 5,817,121. This instrument is manufactured to incorporate at its working end, which is located at the end of the instrument opposite the handle, a tip made of molded plastic mesh gauze. This invention includes an alternate disposable solid instrument and an alternate disposable tubular instrument which will incorporate the mesh plastic tip by molding such mesh plastic onto the working end of the instrument opposite the handle end of the instrument for use in both laparoscopic and conventional surgery.

SUMMARY OF THE INVENTION

The instrument is composed of one or more components which assembled comprise an elongated solid or tubular instrument which can accommodate a one piece, molded, solid or tubular plastic mesh tip. This invention involves a variation of the Christoudias endodissector for dissecting, wiping, or cleaning tissues during endoscopic surgery. The instrument basically includes a head comprising mounting means at one end, an elongated body and a handle at the other end. The instrument includes a mesh plastic body which is mounted securely on the head end portion of the instrument threads or other mounting means.

Accordingly, an object of this invention is to provide a new and improved plastic mesh dissector for endoscopic and/or conventional surgery.

Another object of this invention is to provide a new and improved dissector instrument which is an improvement on the dissector disclosed in U.S. Pat. No. 5,817,121.

BRIEF DESCRIPTION OF THE DRAWINGS

The above and other objects and advantages of this invention may be more clearly seen when viewed in conjunction with the accompanying drawings wherein:

FIG. 1 is a cross sectional view of the endodissector where the plastic mesh dissector is affixed onto the main body of the instrument by screwing the dissector onto said instrument;

FIG. 1a depicts sections of the endodissector shown in FIG. 1 in an exploded view;

FIG. 2 is a cross-sectional view of an alternate embodiment of the invention in which the entire instrument is manufactured as one piece with the head composed of the appropriate plastic such as polypropylene;

FIG. 3 is an alternate embodiment of the invention in which the instrument has a straight central lumen or working port for the insertion of a laparoscopic instrument;

FIG. 4 is an exploded view of the invention shown in FIG. 3;

FIG. 5 is a cross-sectional view of an alternate embodiment of the invention in which the entire instrument as shown in FIG. 3 is manufactured as one piece composed of the appropriate plastic such as polypropylene, and the entire instrument is disposable; and FIG. 6 is a cross-sectional view of an alternate embodiment of the instrument shown in FIG. 5 in which a side port is provided onto which an irrigation aspiration system can be attached.

DETAILED DESCRIPTION OF THE INVENTION

Referring now to the drawing, FIG. 1 shows a plastic mesh dissector 1 attached onto a dissector instrument 2. The "dissector transporter" 2 comprises a main stem 3 with a handle 4 on one end and the plastic mesh dissector 1 on the other. At the headward end of the main stem 3 and along its main axis for a minimum distance of 5 mm there is a recess 5 with sufficient diameter and the receptor threads 6 to accommodate the attaching screw 7 of the dissector 1.

The plastic mesh dissector 1 is secured by threading its attaching screw 7 into the receptor threads 6 of the main stem 3. At the headward end of the main stem 3 there is a tubular recess 31 that will house the body or frame 8 of the plastic mesh dissector 1 and ready the instrument for operation. The dissector 1 comprises two elements; a frame 8 and an enlarged body of plastic mesh 9. FIG. 1 shows the plastic mesh dissector 1 separated from the dissector transporter after unscrewing the attaching screw 7 from the receptor threads 6.

FIG. 2 shows a one piece disposable instrument comprised of plastic gauze dissector 10, a main stem 11 and a handle 12. In this embodiment the dissector 10 and the stem 11 and handle 12 are a unitary structure.

FIG. 3 shows a plastic mesh dissector 13 having an axial aperture 16 attached onto a tubular dissector transporter instrument 14 having a mating axial aperture 19. The tubular plastic mesh dissector 13 comprises a frame 21 with a central lumen 15 and a plastic mesh 18 mounted on the frame 21. On the handleward portion of the tubular plastic mesh dissector 13 there are male threads 17 which secure the tubular plastic mesh dissector 13 onto the tubular dissector transport instrument 14 by engaging the female threads 16 of the tubular transport instrument; the assembled instrument forms a common straight lumen 20 which is used as working port for the insertion of a laparoscopic instrument.

FIG. 4 shows an exploded perspective view of the instrument of FIG. 3 in the unassembled state with the mesh dissector unthreaded from the transporter instrument 14.

FIG. 5 shows the disposable tubular gauze dissector 30 manufactured as one piece. It is comprised of the plastic mesh dissector tip 21, the stem 22 and the straight working port 23 which is the common straight lumen 23 of the plastic mesh dissector 21 and the stem 22.

FIG. 6 shows the disposable tubular gauze dissector of FIG. 5 with the addition of a side port 24 with a lumen 25. This lumen 25 communicates with the straight working port 23 of the instrument. The side port 24 is used for the attachment of an irrigation aspiration device.

While the invention has been explained by a detailed description of certain specific embodiments, it is understood that various modifications and substitutions can be made in any of them within the scope of the appended claims which are intended also to include equivalents of such embodiments.

What is claimed is:

1. An endodissector for dissecting, wiping, and cleaning tissues during laparoscopic or conventional surgery comprising:

an endodissector having a main stem, a first end on said stem having an integral tip located thereon and a second end on said stem having a handle extending along said stem for a predetermined distance and being of a uniform diameter; and, wherein the integral tip comprises a molded non-absorbent plastic mesh on the same axis as the stem and wherein the endodissector is of such dimensions that are compatible with laparoscopic surgery.

2. An endodissector for dissecting, wiping, and cleaning tissues during laparoscopic or conventional surgery in accordance with claim 1 wherein:

the endodissector tip comprises an integral tip of molded non-adsorbent plastic mesh mounted on one end of said stem and a handle mounted axially along and about said stem at the other end of said stem.

3. An endodissector for dissecting, wiping, and cleaning tissues during laparoscopic or conventional surgery in accordance with claim 1 wherein:

the first end on said stem comprises a base having one end with the integral tip mounted thereon an intermediate cylindrical portion and a second end having a threaded portion extending downwardly from the intermediate portion of the base and, wherein, the stem includes an intermediate hollow cylindrical portion having a recess to receive the base intermediate portion and including an end wall having a treaded internal portion to engage the threaded portion extending downwardly from the base to secure the base to the intermediate portion of the stem.

* * * * *